United States Patent [19]

Clemence et al.

[11] Patent Number: 4,719,224

[45] Date of Patent: Jan. 12, 1988

[54] ANTI-INFLAMMATORY AND ANALGESIG THIOPHENE ACETIC ACID DERIVATIVES, COMPOSITIONS, AND METHOD OF USE THEREFOR

[75] Inventors: Francois Clemence; Odile Le Martret, both of Paris; Francoise Delevallee, Fontenay-sous-Bois, all of France

[73] Assignee: Roussel Uclaf, Paris, France

[21] Appl. No.: 836,844

[22] Filed: Mar. 6, 1986

[30] Foreign Application Priority Data

Mar. 12, 1985 [FR] France ................ 85 03584

[51] Int. Cl.$^4$ .................. A61K 31/38; C07D 401/12; C07D 413/12; C07D 333/78

[52] U.S. Cl. .................. 514/443; 514/278; 514/409; 549/43; 548/407; 546/15; 544/146; 544/375

[58] Field of Search ............ 549/43; 548/407; 546/15; 544/146, 375; 514/278, 409, 443

[56] References Cited

FOREIGN PATENT DOCUMENTS 2346348 10/1977 France ................ 549/58

OTHER PUBLICATIONS

Shen et al, *The Development of Antiasthma Drug*, Part III, ed, Butterworth Publishers, Kent, England, 1980.
Stanetty, CA vol. 95, 1981, 95:61895d.

*Primary Examiner*—Alan L. Rotman
*Assistant Examiner*—J. G. Mullins
*Attorney, Agent, or Firm*—Bierman & Muserlian

[57] ABSTRACT

Novel optically active isomers or racemic mixtures of thiophene acetic acid derivatives of the formula

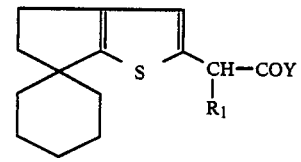

wherein $R_1$ is selected from the group consisting of hydrogen and alkyl of 1 to 5 carbon atoms, Y is selected from the group consisting of $-OR_2$ and

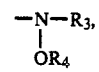

$R_2$ is selected from the group consisting of hydrogen, alkyl of 1 to 5 carbon atoms and

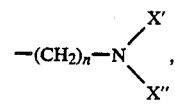

n is an integer from 2 to 5, X' and X" are individually selected from the group consisting of hydrogen and alkyl of 1 to 5 carbon atoms or taken together with the nitrogen atom form an optionally unsaturated heterocycle of 5 to 6 ring members, $R_3$ and $R_4$ are individually selected from the group consisting of hydrogen and alkyl of 1 to 5 carbon atoms and their non-toxic, pharmaceutically acceptable salts with acids and bases having a good analgesic and anti-inflammatory activity and inhibition of 5-lipoxygenase and cyclooxygenase, a process and intermediates for their preparation.

22 Claims, No Drawings

ANTI-INFLAMMATORY AND ANALGESIC THIOPHENE ACETIC ACID DERIVATIVES, COMPOSITIONS, AND METHOD OF USE THEREFOR

Related compounds are described in French patent No. 2,346,348 and Chem. Abs., Vol. 95 No. 7 (1981) p. 689, No. 61895d.

OBJECTS OF THE INVENTION

It is an object of the invention to provide the novel compounds of formula I and their salts and a novel process and intermediates for their preparation.

It is another object of the invention to provide novel analgesic and anti-inflammatory compositions and to a novel method of relieving pain and inflammation in warm-blooded animals.

These and other objects and advantages of the invention will become obvious from the following detailed description.

THE INVENTION

The novel compounds of the invention are selected from the group consisting of optically active isomers or racemic mixtures of thiophene acetic acid derivatives of the formula

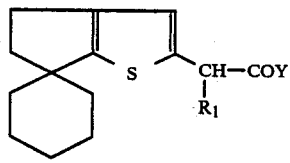

wherein $R_1$ is selected from the group consisting of hydrogen and alkyl of 1 to 5 carbon atoms, Y is selected from the group consisting of $-OR_2$ and

$R_2$ is selected from the group consisting of hydrogen, alkyl of 1 to 5 carbon atoms and

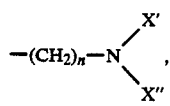

n is an integer from 2 to 5, X' and X" are individually selected from the group consisting of hydrogen and alkyl of 1 to 5 carbon atoms or taken together with the nitrogen atom form an optionally unsaturated heterocycle of 5 to 6 ring members, $R_3$ and $R_4$ are individually selected from the group consisting of hydrogen and alkyl of 1 to 5 carbon atoms and their non-toxic, pharmaceutically acceptable salts with acids and bases.

Examples of $R_1$, $R_2$, $R_3$ and $R_4$ as alkyl of 1 to 5 carbon atoms are methyl, ethyl, isopropyl, n-propyl, n-butyl, n-pentyl, isobutyl and tert.-butyl. $R_1$ is preferably methyl. n is preferably 2 or 3 and X' and X" are preferably hydrogen, methyl or ethyl. Examples of heterocycles when X' and X" are taken together with the nitrogen atoms are piperidinyl, pyrrolidinyl, piperazinyl and morpholinyl.

Examples of acids for the formation of non-toxic, pharmaceutically acceptable acid addition salts are mineral acids such as hydrochloric acid, hydrobromic acid, hyroiodic acid, nitric acid, sulfuric acid and phosphoric acid and organic acids such as formic acid, acetic acid, propionic acid, benzoic acid, citric acid, oxalic acid, glyoxylic acid, tartaric acid, aspartic acid, alkanesulfonic acids such as methanesulfonic acid and ethanesulfonic acid, arylsulfonic acids such as benzene sulfonic acid, p-toluene sulfonic acid and arylcarboxylic acids.

Examples of suitable bases to form non-toxic, pharmaceutically acceptable salts are alkali metal hydroxides or carbonates such as sodium hydroxide and potassium carbonate and amines such as triethylamine and dimethylamine.

A preferred compound is 4',5'-dihydro-α'-methyl-spiro[cyclohexane-1,6'-6H-[cyclopenta (b) thiophene]-2'-acetic acid in optically active form or in racemic mixtures and its salts.

The novel process of the invention for the preparation of the compounds of formula I comprises reducing a spiro[cyclohexane-1,6'-6H-[cyclopenta (b) thiophene]-4'-(5'-H)-one of the formula

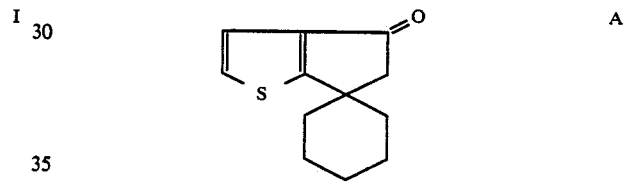

to obtain a 4',5'-dihydro-spiro [cyclohexane-1,6']-6H-[cyclopenta (b) thiophene] of the formula

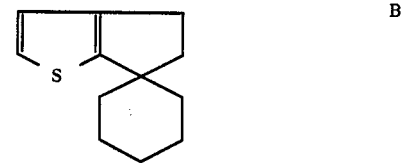

reacting the latter in the presence of a Lewis acid with a derivative of acid of the formula

wherein R' is alkyl of 1 to 5 carbon atoms to obtain a compound of the formula

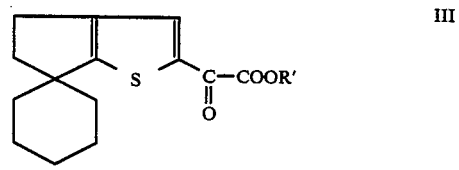

saponifying the latter to obtain 4',5'-dihydro-α'-oxo-spiro[cyclohexane-1,6']-6H-[cyclopenta(b)thiophene]-acetic acid of the formula

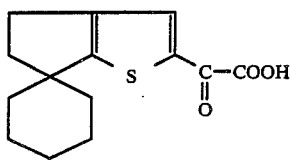

C

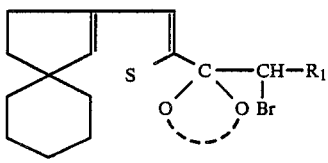

VI and either reducing the keto group to form a methylene to obtain the compound of formula I wherein $R_1$ and $R_2$ are hydrogen or reacting the compound of formula C with an organomagnesium halide of the formula $XMgR_1$ wherein X is halogen and $R_1$ is alkyl of 1 to 5 carbon atoms to obtain a magnesium salt of the formula

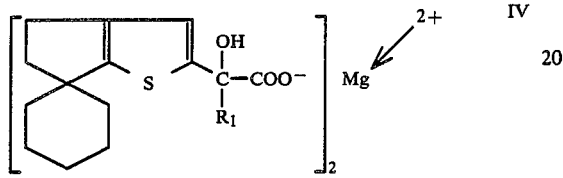

IV and reducing the latter to form the compounds of formula I wherein $R_1$ is alkyl of 1 to 5 carbon atoms and Y is $-OR_2$ and $R_2$ is hydrogen and optionally esterifying the latter to obtain a compound of formula I wherein $R_2$ is alkyl of 1 to 5 carbon atoms or

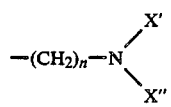

and optionally reacting the said compounds of formula I with a hydroxylamine of the formula $R_3-NH-OR_4$ wherein $R_3$ and $R_4$ have the above definition to obtain the compound of formula I where Y is

which can optionally be resolved by usual methods or transformed into salts by reaction with a base or an acid.

In a variation of the process of the invention, a compound of formula B is reacted in the presence of a Lewis acid with a bromated compound of the formula

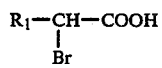

II' wherein $R_1$ has the above definition to obtain a compound of the formula

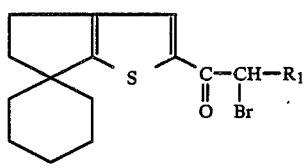

V reacting the latter with a diol in an acid medium to obtain a cyclic acetal of the formula wherein the dotted line represents the remainder of the diol, heating the latter in a polar solvent to obtain an ester of the formula

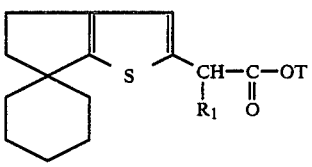

VII wherein T is the remainder of the diol depending on the polar solvent and saponifying the latter to obtain the compound of formula I wherein Y is —OH and optionally treating the latter as described above.

In a preferred mode of the process, the compound of formula II is the acid chloride although other acid halides or acid anhydride may be used and R′ in the acid is preferably methyl or ethyl. The Lewis acid is preferably aluminum chloride although other Lewis acids such as stannic chloride, zinc chloride, boron trifluoride and phosphoric acid may be used.

The saponification of the compounds of formula III may be effected under the usual conditions and the reduction of the carbonyls in the compounds of formulae A and C is preferably effected by a Wolff-Kishner reaction in the presence of hydrazine hydrate, ethyleneglycol and potassium hydroxide.

The organomagnesium halide is preferably methyl magnesium iodide and the reaction is preferably effected in the presence of a mixture of ether and tetrahydrofuran. The reduction of the magnesium salt of formula IV is preferably with stannous chloride but other reductions such as catalytic hydrogenation may be used.

The esterification of the acids of formula I can be effected by known methods by reaction with an alcohol, aminoalcohol, alkyl halide or aminoalkyl halide or with diazomethane for methylation. For the compounds of formula I wherein Y is

the compounds of formula I wherein Y is —OH is reacted with hydroxylamine hydrochloride or one of its derivatives in an organic solvent such as methylene chloride after activation of the carboxyl group in the presence of carbonyldiimidazole preferably.

In the process variation, the compound of formula II' is preferably in the α-bromated acid chloride form and is reacted under the same conditions as the acid of formula II with compound B. The compound of formula V is preferably reacted at reflux with 2,2-dimethyl-1,3-propanediol in an organic solvent such as toluene in the presence of an acid such as p-toluene sulfonic acid to form the cyclic acetal of formula VI. The acetal is preferably heated in a polar solvent at a temperature between 50° C. and the reflux temperature of the solvent. The preferred polar solvent is an optionally substituted ethanediol and the reaction is effected in the presence of an alkali metal acetate catalyst such as potassium acetate. T in the compounds of formula VII will depend on the diol and polar solvent used and may be a mixture of esters. The saponification of the compounds of formula VII may be effected under the usual conditions.

The novel analgesic and anti-inflammatory compositions of the invention are comprised of an analgesically and anti-inflammatorily effective amount of at least one compound of formula I and their non-toxic, pharmaceuticlly acceptable salts and an inert pharmaceutical carrier. The compositions may be in the form of tablets, dragees, gelules, capsules, granules, suppositories, injectable solutions or suspensions, pommades, creams, gels and aerosol preparations.

Examples of suitable excipients are talc, arabic gum, lactose, starch, magnesium stearate, cacao butter, aqueous and non-aqueous vehicles, animal and vegetable fats, paraffinic derivatives, glycols, various wetting agents, dispersants or emulsifiers and preservatives.

The compositions have a good analgesic and anti-inflammatory activity and also an important anti-arthritic power as well as an important inhibiting activity of 5-lipoxygenase and cyclooxygenase. The compositions are therefore useful in the treatment of degenerative inflammatory conditions such as osteoarthrosis, diverse collagenosis such as tendinitis, etc., of rhumatic conditions such as rhumatoid polyarthritis or ankylosant spondylarthritis as well as other conditions of an auto immune nature such as dissemine erythrematous lupus, glomerulonephritis, sclerosis in plates, etc.

The compositions of the invention are also useful for the treatment of muscular, articular or nervous pain, dental pain, migraines and zona as well as a complementary treatment of infections and febrile states. They are also useful for the treatment of psoriasis, asthma and certain cardiovascular disorders such as myocardia infractions. The preferred compositions contain optically active isomers or racemates of 4',5'-dihydro-α'-methyl-spiro[cyclohexane-1,6']-6H-[cyclopenta (b) thiophene]-acetic acid and its non-toxic, pharmaceutically acceptable salts of a base.

The novel method of relieving pain and inflammation in warm-blooded animals, including humans, comprises administering to warm-blooded animals an analgesically and anti-inflammatorily effective amount of at least one compound of formula I and their non-toxic, pharmaceutically acceptable salts. The compounds may be administered orally, rectally, parenterally or topically to the skin and mucous. The usual daily dose is 0.275 to 27.5 mg/kg depending on the condition treated, the method of administration and the specific compound.

The novel intermediates of the invention are the compounds of formulae III, IV, V and VI and the preferred intermediates are 4',5'-dihydro-spiro[cyclohexane-1,6']-6H-[cyclopenta (b) thiophene] and 4',5'-dihydro-α'-oxo-spiro[cyclohexane-1,6']-6H-[cyclopenta (b) thiophene]-2'-acetic acid.

In the following examples there are described several preferred embodiments to illustrate the invention. However, it should be understood that the invention is not intended to be limited to the specific embodiments.

EXAMPLE 1

4',5'-dihydro-α'-methyl-spiro[cyclohexane-1,6']-6H-[cyclopenta (b) thiophene]-2'-acetic acid STEP A: 4',5'-dihydro-spiro[cyclohexane-1,6']-6H-[cyclopenta (b) thiophene]

19.9 ml of a solution of 700 g of potassium hydroxide per liter of water were added dropwise with stirring at room temperature to a mixture of 17 g of spiro[cyclohexane-1,6']-6H-[cyclopenta (b) thiophene]-4'-(5'-H)-one [prepared by process of Stanelty, J. Chem., Res (S), 1981, p. 99] and 55 ml of ethylene glycol. The temperature was raised to 45° C. and 30.7 ml of hydrazine hydrate were added dropwise to the mixture which was then heated at reflux at 125° C. for one hour. Excess water was distilled at atmospheric pressure and the temperature was increased to reflux at 195° C. After reflux for 3 hours, the mixture was poured into 150 ml of water after which 150 ml of ether were added. The decanted aqueous phase was extreated with ether and the combined organic phases were washed with water until the wash water was neutral, dried, purified with activated carbon, filtered and evaporated to dryness under reduced pressure. The oil residue was chromatographed in a high pressure column and eluted with petroleum ether (b.p.=60° to 80° C.) to obtain 4',5'-dihydro-spiro[cyclohexane-1,6']-6H-[cyclopenta] (b) thiophene as a colorless oil with an Rf=0.6.

Analysis: $C_{12}H_{16}S$; molecular weight=192.3 Calculated: % C 74.95, %H 8.40; %S 16.65; Found: 75.2; 8.6; 16.6.

STEP B: Ethyl 4',5'-dihydro-α'-oxo-spiro[cyclohexane-1,6']-6H-[cyclopenta (b) thiophene]-2'-acetate A solution of 6.9 ml of ethyl chlorooxoacetate in 10 ml of 1,2-dichloroethane was added over 7 minutes at 5° to 6° C. to a mixture of 80 ml of 1,2-dichloromethane and 9 g of aluminum chloride at 0° C. and the mixture was stirred for 15 minutes 0° to 5° C. After cooling the mixture to −5° C., a solution of 10.2 g of the product of Step A in 20 ml of 1,2-dichloroethane was added thereto over 30 minutes. The mixture was stirred at 0° to 5° C. for 4 hours and for 16 hours at 20° C. The solution was poured with stirring into a mixture of 265 ml of ice and water and 53 ml of 22° Bé hydrochloric acid and the mixture was rinsed with 100 ml of methylene chloride. After stirring for one hour, the mixture was extracted with methylene chloride and the organic phase was washed with water and evaporated to dryness under reduced pressure to obtain 14.5 g of ethyl 4',5'-dihydro-α'-oxo-spiro[cyclohexane,-1,6']-6H-[cyclopenta (b) thiophene]-2'-acetate which after chromatography over silica and elution with methylene chloride had an Rf=0.49.

STEP C: 4',5'-dihydro-α'-oxo-spiro[cyclohexane-1,6']-6H-[cyclopenta (b) thiophene]-2'-acetic acid 26.7 ml of 2N sodium hydroxide solution were added dropwise at 18° to 20° C. under argon to a solution of 14.2 g of the product of Step B, 18 ml of ethanol and 36 ml of water and after stirring for 2 hours, 180 ml of water were added. The mixture was filtered and rinsed with water and washed twice with 100 ml of ether. The ether was reextracted with 50 ml of water and the combined aqueous phases were acidified to a pH of 1 with 22° Bé hydrochloric acid in the presence of 150 ml of ethyl acetate. The decanted aqueous phase was extracted twice with 100 ml of ethyl acetate and the organic phase was washed with aqueous sodium hydroxide (70 g/l), dried, treated with activated carbon, filtered and evaporated to dryness under reduced pressure. The resinous residue was empasted with petroleum ether (b.p.=60° to 80° C.), was vacuum filtered, washed with petroleum ether (b.p.=60° to 80° C.) and dried to obtain 10.9 g of 4',5'-dihydro-α'-oxo-spiro[cyclohexane-1,6']-6H-[cyclopenta (b) thiophene]-2'-acetic acid which after chromatography over silica and elution with a 7-2-1 ethyl acetate-ethanol-water mixture had an Rf=0.43.

STEP D: Magnesium salt of 4',5'-dihydro-α'-hydroxy-α'-methyl-spiro[cyclohexane-1,6']-6H-[cyclopenta (b) thiophene]-2'-acetic acid 42 ml of methyl magnesium iodide in ether were added dropwise under argon 6° to 8° C. to a solution of 7.97 g of the product of Step C in 126 ml of tetrahydrofuran and the mixture was stirred at 0° to 5° C. for 45 minutes and then at 20° to 25° C. for two hours. A solution of 18 g of ammonium chloride in 180 ml of water was slowly added to the mixture at 10° to 15° C. and the mixture was evaporated at 20° C. under reduced pressure. The mixture was vacuum filtered and the crystalline product was rinsed with water then with ether and dried to obtain 8.65 g of magnesium salt of 4',5'-dihydro-α'-methyl-spiro[cyclohexane-1,6']-6H-[cyclopenta (b) thiophene]-2'-acetic acid. The acid had a melting point of 160° C.

Analysis: $C_{30}H_{38}O_6S_2Mg$; molecular weight=583.073. Calculated: %C 61.8; %H 6.57; %Mg 4.17; Found: 58.5; 6.8; 4.7.

STEP E: 4',5'-dihydro-α'-methyl-spiro[cyclohexane-1,6']-6H-[cyclopenta (b) thiophene]-2'-acetic acid 8.65 g of the product of Step D were added in small fractions at 18° to 21° C. to a mixture of 10 g of stannous chloride, 15 ml of 22° Bé hydrochloric acid and 28.5 ml of acetic acid and after stirring for 5 hours at 20° to 25° C., the mixture was vacuum filtered. The recovered crystals were rinsed with acetic acid, then with water and dried under reduced pressure at 20° to 25° C. 5.89 g of the said raw product were dissolved at 20° C. in 30 ml of acetic acid and the solution was treated with activated carbon, filtered and rinsed with acetic acid. 19 ml of water were added dropwise to the filtrate at 20° C. to effect crystallization and the mixture was vacuum filtered. The product was rinsed with aqueous 30% acetic acid and dried at 20° C. under reduced pressure to obtain 5.21 g of product which was purified again as above to obtain 4.85 g of 4',5'-dihydro-α'-methyl-spiro[cyclohexane-1,6']-6H-[cyclopenta (b) thiophene]-2'-acetic acid melting at 95° C.

Analysis: $C_{15}H_{20}O_2S$; molecular weight=264.389. Calculated: %C 68.14; %H 7.62; %S 12.13; Found: 68.3; 7.8; 12.0.

EXAMPLE 2

2-dimethylamino-ethyl 4',5'-dihydro-α'-methyl-spiro[cyclohexane-1,6']-6H-[cyclopenta (b) thiophene]-2'-acetate oxalate A suspension of 132 mg of the compound of Example 1, 144 mg of 2-chloro-N,N-dimethylaminoethane hydrochloride, 520 mg of potassium carbonate and 2 ml of dimethylformamide was stirred under argon at 20° to 22° C. for 22 hours and was then poured into 50 ml of water. The mixture was filtered through silica and was rinsed with water. The product was dissolved in methylene chloride and the solution was filtered, dried and evaporated to dryness under reduced pressure. The 55 mg of colorless oil residue were taken up in 0.5 ml of isopropanol and 25 mg of the dihydrate of oxalic acid were added thereto. The mixture was vacuum filtered and the product was rinsed with isopropanol and then with ether to obtain 43 mg of 2-dimethylamino-ethyl 4',5'-dihydro-α'-methyl-spiro[cyclohexane-1,6']-6H-[cyclopenta (b) thiophene]-2'-acetate oxalate melting at 144° C.

Analysis: Calculated: %C 59.27; %H 7.34; %N 3.29; %S 7.53; Found: 59.1; 7.5; 3.2; 7.5.

EXAMPLE 3

Methyl 4',5'-dihydro-α'-methyl-spiro[cyclohexane-1,6']-6H-[cyclopenta (b) thiophene]-2'-acetate 20 ml of a solution of 0.4M diazomethane in methylene chloride was added over 5 minutes 15° to 20° C. to a mixture of 1.5 g of the product of Example 1 in 5 ml of methylene chloride cooled in an ice-water bath and the mixture was extracted with methylene chloride. The organic phase was washed with water, dried, stirred with 2 g of silica for 5 minutes and was filtered. The filtrate was evaporated to dryness under reduced pressure to obtain 1.579 g of methyl 4',5'-dihydro-α'-methyl-spiro[cyclohexane-1,6']-6H-[cyclopenta (b) thiophene]-2'-acetate in the form of a colorless oil with a Rf=0.73 (chromatography over silica-methylene chloride-ethyl acetate (1-1) eluant).

EXAMPLE 4

4',5'-dihydro-α',N-dimethyl-N-hydroxy-spiro[cyclohexane-1,6']-6H-[cyclopenta (b) thiophene]-2-acetamide A mixture of 5.3 g of the product of Example 1, 5.2 g of carbonyldiimidazole and 55 ml of methylene chloride was stirred at room temperature under an inert atmosphere for 30 minutes and after the addition of 3.5 g of N-methyl-hydroxylamine hydrochloride, the mixture was stirred for 72 hours and was filtered. The filtrate was washed with 100 ml of N hydrochloric acid, then with water, dried and evaporated to dryness under reduced pressure. The 6.1 g of residue were chromatographed over silica and eluted with an 8-2 methylene chloride-ethyl acetate mixture to obtain 3.3 g of 4',5'-dihydro-α',N-dimethyl-N-hydroxy-spiro[cyclohexane-1,6']-6H-[cyclopenta (b) thiophene]-2-acetamide with an Rf=0.3.

A solution of 6.75 ml of 32% sodium hydroxide in 27 ml of water were added to a solution of 2.7 g of the above compound in 13.5 ml of 100% ethanol and the mixture was iced for 15 minutes and was vacuum filtered. The crystals were washed with iced water and dried under reduced pressure at room temperature to obtain 1.73 g of the sodium salt of the said product melting at 120° C. (with decomposition).

Analysis: $C_{16}H_{23}NO_2S.3H_2ONa$; molecular weight=369.459 Calculated: %C 52.01; %H 7.64; %S 8.68; %N 3.79; Found: 52.2; 7.5; 8.4; 3.5.

EXAMPLE 5

4',5'-dihydro-N-hydroxy-α-methyl-spiro[cyclohexane-1,6']-6H-[cyclopenta (b) thiophene]-2'-acetamide Using the procedure of Example 4, 4 g of the product of Example 1 and 2.2 g of hydroxylamine hydrochoride were reacted. The mixture was stirred for 5 hours at room temperature and was then filtered. The filtrate was washed with 100 ml of N hydrochloric acid, then with water, dried and evaporated to dryness under reduced pressure. The 4.2 g of crystallized product were empasted with 30 ml of hexane and was vacuum filtered. The product was washed with hexane and dried under reduced pressure and crystallized from ethyl acetate to obtain 2.15 g of 4',5'-dihydro-N-hydroxy-α-methyl spiro[cyclohexane-1,6']-6H-[cyclopenta (b) thiophene]-2'-acetamide melting at 135° C.

Analysis: $C_{15}H_{21}NO_2S$; molecular weight=279.404
Calculated: %C 64.48; %H 7.58; %S 11.48; %N 5.01;
Found: 64.4; 7.7; 11.3; 5.0.

EXAMPLE 6

4',5'-dihydro-N-hydroxy-α'-methyl-N-isopropyl-spiro[cyclohexane-1,6']-6H-[cyclopenta (b) thiophene]-2'-acetamide Using the procedure of Example 4, 4 g of the product of Example 1 and 3.55 g of N-isopropyl-hydroxylamine hydrochloride were reacted for 90 minutes and after chromatography over silica and elution with methylene chloride, 4.4 g of 4',5'-dihydro-N-hydroxy-α-methyl-N-isopropyl-spiro[cyclohexane-1,6']-6H-[cyclopenta (b) thiophene]-2'-acetamide in the form of an oil were obtained.

Analysis: $C_{18}H_{27}NO_2S$; molecular weight=321.486
Calculated: %C 67.25; %H 8.47; %S 9.97; %N 4.36;
Found: 67.2; 8.5; 9.9; 4.4.

EXAMPLE 7

4',5'-dihydro-α,N-dimethyl-N-methoxy-spiro[cyclohexane-1,6']-6H-[cyclopenta (b) thiophene]-2'-acetamide Using the procedure of Example 4, 4 g of the product of Example 1 and 3.1 g of methoxymethylamine hydrochloride were reacted for 20 hours and after chromatography over silica and elution with an 8-2 methylene chloride-ethyl acetate mixture, 3.65 g of 4',5'-dihydro-α,N-dimethyl-N-methoxy-spiro[cyclohexane-1,6']-6H-[cyclopenta (b) thiophene]-2'-acetamide with an Rf=0.6 were obtained.

Analysis: $C_{17}H_{25}NO_2S$; molecular weight=307.459
Calculated: %C 66.41; %H 8.20; %S 10.43; %N 4.55;
Found: 66.5; 8.4; 10.1; 4.4.

EXAMPLE 8

4',5'-dihydro-spiro[cyclohexane-1,6'-]-6H-[cyclopenta (b) thiophene]-2'-acetic acid A solution of 5 g of the product of Step C of Example 1 in 3.7 ml of hydrazine hydrate was added at 40° C. to a solution of 4.25 g of potassium hydroxide in 36 ml of diethyleneglycol and the mixture was progressively heated to 200° C. while distilling water. The mixture was heated with stirring at 200° C. for 90 minutes and was then returned to room temperature. The mixture was poured into 100 ml of water and the aqueous phase was washed with 200 ml of ethyl acetate. 15 ml of concentrated hydrochloric acid were added to the aqueous phase which was then extracted with ethyl acetate. The combined organic phases were washed with water, dried, treated with activated carbon, filtered and evaporated to dryness under reduced pressure. The 5.29 g of crystallized residue were empasted with hexane and vacuum filtered. The product was dried under reduced pressure to obtain 3.26 g of 4',5'-dihydro-spiro[cyclohexane-1,6']-6H-[cyclopenta (b) thiophene]-2'-acetic acid which melted at 92° C. after crystallization from hexane.

Analysis: $C_{14}H_{18}O_2S$; molecular weight=250.362
Calculated: %C 67.16; %H 7.25; %S 12.81; Found: 67.2; 7.3; 12.5.

EXAMPLE 9

4',5'-dihydro-α-methyl-spiro[cyclohexane-1,6']-6H-[cyclopenta (b) thiophene]-2'-acetic acid STEP A: 2-bromo-1-[4',5'-dihydro-spiro[cyclohexane-1,6']-6H-(cyclopenta) (b) thiophene)-2'-yl]-1-propanone 8.7 g of aluminum chloride were dissolved in 80 ml of hot 1,2-dichloroethane and after cooling to 0° C., a solution of 10.28 g of α-bromo-propionyl chloride in 30 ml of 1,2-dichloroethane were added over 5 minutes at 0° C. A solution of 9.61 g of spiro[cyclohexane-1,6']-6H-[cyclopenta (b) thiophene]-4'-(5'H)-one in 20 ml of 1,2-dichloroethane was added thereto over 15 minutes at 0° to 5° C. and the temperature was allowed to rise to room temperature. The mixture was refluxed for one hour, was cooled and 200 ml of N hydrochloric acid were added thereto. The organic phase was washed with water, heated with activated carbon, filtered and evaporated to dryness under reduced pressure. The 16.52 g of residue were taken up in 50 ml of hexane and the solution was refluxed, allowed to cool and was vacuum filtered to obtain 11.77 g of 2-bromo-1-[4',5'-dihydro-spiro[cyclohexane-1,6']-6H-(cyclopenta (b) thiophene)-2'-yl]-propanone melting at 50° C.

STEP B: 2-(1-bromoethyl)-2-[4',5'-dihydro-spiro(cyclohexane-1,6')-6H-(cyclopenta (b) thiophene)-2'-yl]-1,3-dioxane A mixture of 5 g of the product of Step A, 3.12 g of 2,2-dimethyl-1,3-propanediol, 0.28 g of p-toluene sulfonic acid and 20 ml of toluene was refluxed for 5½ hours while distilling the water of reaction formed and was then cooled and filtered. The organic phase was washed with aqueous 10% sodium carbonate solution, with water, dried and evaporated to dryness under reduced pressure to obtain 5.95 g of 2-(1-bromoethyl)-2-[4',5'-dihydro-spiro(cyclohexane-1,6')-6H-(cyclopenta (b) thiophene)-2'-yl]-1,3-dioxane which was used as is for the next step.

STEP C: 4',5'-dihydro-α-methyl-spiro[cyclohexane-1,6']-6H-[cyclopenta (b) thiophene]-2'-acetic acid A mixture of 2.06 g of the product of Step B, 0.5 g of potassium acetate and 25 ml of 1,2-ethanediol was heated at 125° C. for 5 hours and was cooled and poured into 50 ml of water. The mixture was extracted with ethyl acetate and the organic phase was dried and evaporated to dryness under reduced pressure to obtain 1.6 g of an ester. The product was added to 5 ml of methanol and 1 ml of sodium hydroxide and the mixture was refluxed for 90 minutes. The methanol was distilled and 10 ml of water were added. The mixture was extracted with methyl ethyl ketone and the aqueous phase was acidified to a pH of 1 by addition of concentrated hydrochloric acid. The mixture was extracted again and the combined organic phases were washed with water, dried and evaporated to dryness under reduced pressure to obtain 1.15 g of 4',5'-dihydro-2-methyl-spiro[cyclohexane-1,6']-6H-[cyclopenta (b) thiophene]-2'-acetic acid identical to that obtained in Example 1.

EXAMPLE 10

Tablets were prepared containing 50 mg of the compound of Example 1 and sufficient excipient of lactose, talc, starch and magnesium stearate for a final weight of 350 mg.

PHARMACOLOGICAL DATA

A. Anti-inflammatory Activity-adjuvant arthritis (preventive treatment)

The injection of Freund type adjuvant into the rear paw of a rat provokes the rapid appearance of a primary inflammatory lesion in that paw and then after a latent period of 13 to 15 days, the appearance of a secondary arthritic condition occurs in the other rear paw The test was performed on male rats about 40 to 50 days old who received an intraplantary injection of 0.1 ml of Freund type adjuvant (suspension of 6 mg per ml of dead mycobacterium butyrium in vaseline oil). The rats received the test compound orally on day 0 (day of injection of adjuvant) until the day before they were killed (day 17). The arthritic control animals and the normal control animals did not receive the vehicle. The activity of the test compounds was determined by the increase in the injected rear paw volume (primary and secondary inflammation) and the non-injected rear paw (secondary inflammation) as compared to the average volume of the corresponding paws of the arthritic control animals. The $DA_{50}$ or the dose that diminished by 50% the volume increase of the rear paws of the treated animals as compared to the control animals was determined to be 8 mg/kg for the compound of Example 1.

B. Inhibition of biosynthesis of prostaglandins in vitro

Arachidonic acid is converted into prostaglandins (PGs) of the Z series by a cyclo-oxygenase contained in a microsomal preparation of seminal vesicules of bulls by the method of Tagekuchi et al [Biochemistry, Vol. 10 (1971), P. 2372]. The precursor at a concentration of $15 \times 10^{-6}$ M was incubated in the presence of a fixed concentration of proteins of the seminal vesicule preparation and the test product at 37° C. for 30 minutes. The reaction was stopped by immersion into boiling water for one minute and then centrifugation. The prostaglandins were determined by radio-immunoassay by the procedure of Dray et al [European J. Clin. Invest., Vol. 5 (1975), p. 311] to specifically evaluate for $PGE_2$ and $PGF_2\alpha$. The $CI_{50}$ dose or dose that inhibited the activity by 50% was calculated for each of the two prostaglandins and was $2 \times 10^{-5}$ M for the compound of Example 1.

3. Dosage of 5-lipoxygenase of rat neutrophiles

Peritoneal neutrophile ($5 \times 10^6$ cells/ml) obtained after intraperitoneal injection of 12% sodium caseinate were preincubated at 37° C. for 5 minutes in the presence of the test product or solvent used. The incubation was effected under the same conditions in the presence of 10 μM of ionophore A 23187 and 5 ml of calcium chloride. After 5 minutes, the incubates were placed in ice and centrifuged at 3000 g. Leucotriene $B_4$ is determined in the surnageant by radioimmuno assay and the results are reported in the following Table.

TABLE

| Product of Example | $CI_{50}$ 5-lipoxygenase | cyclooxygenase |
|---|---|---|
| 1 | $1 \times 10^{-5}$ M | $2 \times 10^{-5}$ M |
| 4 | $0.5 \times 10^{-6}$ M | $2 \times 10^{-4}$ M |

Various modifications of the products and methods of the invention may be made without departing from the spirit or scope thereof and it is to be understood that the invention is intended to be limited only as defined in the appended claims.

What is claimed is:

1. A compound selected from the group consisting of optically active isomers or racemic mixtures of thiophene acetic acid derivatives of the formula

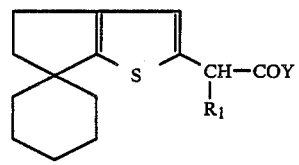

wherein $R_1$ is selected from the group consisting of hydrogen and alkyl of 1 to 5 carbon atoms, Y is selected from the group consisting of —$OR_2$ and

$R_2$ is selected from the group consisting of hydrogen, alkyl of 1 to 5 carbon atoms and

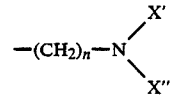

is an integer from 2 to 5, X' and X" are individually selected from the group consisting of hydrogen and alkyl of 1 to 5 carbon atoms, $R_3$ and $R_4$ are individually selected from the group consisting of hydrogen and alkyl of 1 to 5 carbon atoms and their non-toxic, pharmaceutically acceptable salts with acids and bases.

2. A compound of claim 1 selected from the group consisting of 4',5'-dihydro-α'-methyl-spiro[cyclohexane-1,6']-6H-[cyclopenta (b) thiophene]-2'-acetic acid in its optically active or racemic form and its salts of a non-toxic, pharmaceutically acceptable base.

3. A compound of claim 1 selected from the group consisting of 2-(dimethylamino)-ethyl 4',5'-dihydro-α'-methyl-spiro[cyclohexane-1,6']-6H-[cyclopenta (b) thiophene]-2'acetate and its non-toxic, pharmaceutically acid addition salts.

4. A compound of claim 1 which is methyl 4',5'-dihydro-α'-methyl-spiro[cyclohexane-1,6']-6H-[cyclopenta (b) thiophene]-2 α -acetate.

5. A compound of claim 1 selected from the group consisting of 4',5'-dihydro-α'-N-dimethyl-N-hydroxy-spiro[cyclohexane-1,6']-6H-[cyclopenta (b) thiophene]-2'-acetamide and its salts of non-toxic, pharmaceutically acceptable bases.

6. A compound of claim 1 selected from the group consisting of 4',5'-dihydro-N-hydroxy-α'-methyl-spiro[cyclohexane-1,6']-6H-[cyclopenta (b) thiophene]-2'- acetamide and its salts of non-toxic, pharmaceutically acceptable bases.

7. A compound of claim 1 selected from the group consisting of 4′,5′-dihydro-N-hydroxy-α′-methyl-N-isopropyl-spiro[cyclohexan 1,6′-6H-[cyclopenta (b) thiophene]-2′-acetamide and its salts of non-toxic, pharmaceutically acceptable bases.

8. A compound of claim 1 selected from the group consisting of 4′,5′-dihydro-spiro[cyclohexane-1,6′]-6H-[cyclopenta (b) thiophene]-2′-acetic acid in its optically active or racemic form and its salts of non-toxic, pharmaceutically acceptable bases.

9. A compound selected from the group consisting of 4′,5′-dihydro-α,N-dimethyl-N-methoxy-spiro[cyclohexane-1,6′]-6H-[cyclopenta (b) thiophene]-2′-acetamide and its non-toxic, pharmaceutically acceptable salts.

10. A compound having a formula selected from the group consisting of

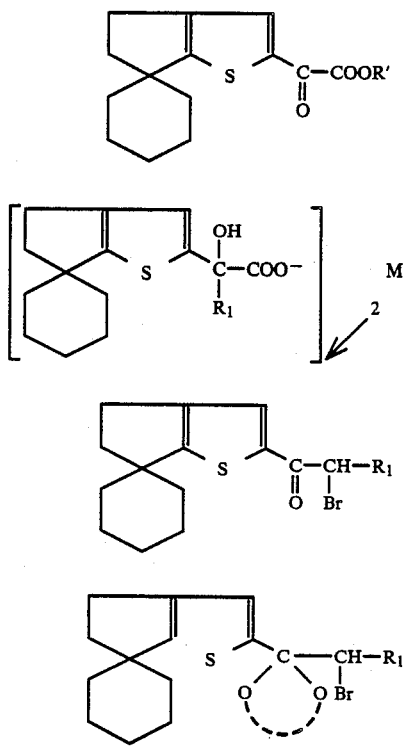

wherein R′ and R₁ are alkyl of 1 to 5 carbon atoms.

11. A compound selected from the group consisting of spiro4′,5′-dihydro-[cyclohexane-1,6′[-6H-[cyclopenta (b) thiophene] and 4′,5′-dihydro-α′-oxo-spiro[-cyclohexane 1,6′]-6H-[cyclopenta (b) thiophene]-2′-acetic acid.

12. An analgesic and anti-inflammatory composition comprising an analgesically and anti-inflammatorily effective amount of at least one compound of claim 1 and an inert pharmaceutical carrier.

13. A composition of claim 12 selected from the group consisting of 4′,5′-dihydro-α′-methyl-spiro[cyclohexane-1,6′]-6H-[cyclopenta (b) thiophene]-2′-acetic acid in its optically active or racemic form and its salts of non-toxic, pharmaceutically acceptable base.

14. A method of relieving pain and inflammation in warm-blooded animals comprising administering to warm-blooded animals an analgesically and anti-inflammatorily effective amount of at least one compound of claim 1.

15. A method of claim 14 wherein the active compound is selected from the group consisting of 4′,5′-dihydro-α′-methyl-spiro[cyclohexane-1,6′]-6H-[cyclopenta (b) thiophene]-2′-acetic acid in its optically active or racemic form and its salts of non-toxic,pharmaceutically acceptable bases.

16. A method of claim 14 wherein the active compound is selected from the group consisting of 2-(dimethylamino)-ethyl 4′,5′-dihydro-α′-methyl-spiro[cyclohexane-1,6′]-6H-[cyclopenta (b) thiophene]-2′-acetate and its non-toxic, pharmaceutically acid addition salts.

17. A method of claim 14 wherein the active compound is methyl 4′,5′-dihydro-α′-methyl-spiro[cyclohexane-1,6′]-6H-[cyclopenta (b) thiophene]-2′-acetate.

18. A method of claim 14 wherein the active compound is selected from the group consisting of 4′,5′-dihydro-α′-N-dimetyl-N-hydroxy-spiro[cyclohexane-1,6′-6H-[cyclopenta (b) thiophene]-2′-acetamide and its salts of non-toxic, pharmaceutically acceptable bases.

19. A method of claim 14 wherein the active compound is 4′,5′-dihydro-N-hydroxy-α′-methyl-spiro[cyclohexane-1,6′]-6H-[cyclopenta (b) thiophene]-2′-acetamide and its salts of non-toxic, pharmaceutically acceptable bases.

20. A method of claim 14 wherein the active compound is 4′,5′-dihydro-N-hydroxy-α′-methyl-N-isopropyl-spiro[cyclohexane-1,6′]-6H-[cyclopenta (b) thiophene]-2′-acetamide and its salts of non-toxic, pharmaceutically acceptable bases.

21. A method of claim 14 wherein the active compound is selected from the group consisting of 4′,5′-dihydro-spiro[cyclohexane-1,6′]-6H-[cyclopenta (b) thiophene]-2′-acetic acid in its optically active or racemic form and its salts of non-toxic, pharmaceutically acceptable base.

22. A method of claim 14 wherein the active compound is selected from the group consisting of 4′,5′-dihydro-α′-N-dimethyl-N-methoxy-spiro[cyclohexane-1,6′]-6H-[cyclopenta (b) thiophene]-2′-acetamide and its non-toxic, pharmaceutically acceptable salts.

* * * * *